(12) United States Patent
Fisher et al.

(10) Patent No.: US 8,062,797 B2
(45) Date of Patent: Nov. 22, 2011

(54) ARTICLES OF CLOTHING AND PERSONAL GEAR WITH ON-DEMAND POWER SUPPLY FOR ELECTRICAL DEVICES

(75) Inventors: Tobin J. Fisher, San Francisco, CA (US); Thomas C. Covington, San Francisco, CA (US); Jonathan L. Glassman, Indianapolis, IN (US); Jesse M. Thomas, San Francisco, CA (US); Daniel Braithwaite, Rowland Heights, CA (US)

(73) Assignee: Ardica Technologies, Inc., San Francisco, CA (US)

( * ) Notice: Subject to any disclaimer, the term of this patent is extended or adjusted under 35 U.S.C. 154(b) by 1480 days.

(21) Appl. No.: 11/124,401

(22) Filed: May 6, 2005

(65) Prior Publication Data

US 2005/0255349 A1    Nov. 17, 2005

Related U.S. Application Data

(60) Provisional application No. 60/569,340, filed on May 7, 2004.

(51) Int. Cl.
*H01M 8/04* (2006.01)
*A41D 1/04* (2006.01)

(52) U.S. Cl. ........ 429/400; 429/492; 429/507; 429/513; 429/468; 2/102; 2/905; 219/211

(58) Field of Classification Search ............... 429/34, 429/18, 32, 12, 127; 2/905, 102, 108; 219/211
See application file for complete search history.

(56) References Cited

U.S. PATENT DOCUMENTS

| | | | |
|---|---|---|---|
| 3,774,589 A | 11/1973 | Kober | |
| 4,846,176 A | 7/1989 | Golden | |
| 5,817,157 A | 10/1998 | Checketts | |
| 5,973,602 A | 10/1999 | Cole, III et al. | 340/584 |
| 6,045,575 A | 4/2000 | Rosen et al. | 607/88 |
| 6,127,058 A | 10/2000 | Pratt et al. | 429/30 |
| 6,250,078 B1 | 6/2001 | Amendola | |

(Continued)

FOREIGN PATENT DOCUMENTS

JP    2004-362805    12/2004

(Continued)

OTHER PUBLICATIONS

D.J. Laser and J.G. Santiago, "A Review of Micropumps", J. Micromech. Microeng.; vol. 14 (2004) R35-R64.

(Continued)

*Primary Examiner* — Raymond Alejandro
(74) *Attorney, Agent, or Firm* — Jeffrey Schox (57) ABSTRACT

An article of clothing with an on-demand power supply for electrical devices is provided. The power supply includes stiff planar fuel cell devices that are distributed in a plane. The number of fuel cells is dependent on the power requirements for the electrical devices. The planar stiff fuel cells are flexibly interconnected in the plane by a flexible interconnection, which allows the fuel cells to move with respect to each other out of the plane. This further allows the power supply to be nicely integrated in an article of clothing and minimizes negative impact to a body region or to the article of clothing. The electrical and fuel connections between the fuel cells are integrated with the flexible interconnection. To further integrate and increase ease of operation a control system is included to control the on-demand power supply or control power levels for the electrical device.

15 Claims, 9 Drawing Sheets

U.S. PATENT DOCUMENTS

| | | | |
|---|---|---|---|
| 6,268,077 B1 | 7/2001 | Kelley et al. | 429/33 |
| 6,268,595 B1 | 7/2001 | Haenel | 219/528 |
| 6,289,888 B1 | 9/2001 | Welles | 126/263.01 |
| 6,326,097 B1 | 12/2001 | Hockaday | |
| 6,375,638 B2 | 4/2002 | Nason | |
| 6,392,313 B1 | 5/2002 | Epstein | |
| 6,433,129 B1 | 8/2002 | Amendola | |
| 6,468,694 B1 | 10/2002 | Amendola | |
| 6,497,973 B1 | 12/2002 | Amendola | |
| 6,524,542 B2 | 2/2003 | Amendola | |
| 6,534,033 B1 | 3/2003 | Amendola | |
| 6,544,400 B2 | 4/2003 | Hockaday | |
| 6,544,679 B1 | 4/2003 | Petillo | |
| 6,579,068 B2 | 6/2003 | Bridger | |
| 6,586,563 B1 | 7/2003 | Ortega | |
| 6,589,681 B1 | 7/2003 | Yamanis | 429/34 |
| 6,620,542 B2 | 9/2003 | Pan | 429/41 |
| 6,645,651 B2 | 11/2003 | Hockaday | |
| 6,660,421 B2 | 12/2003 | Merin Celemin et al. | 429/34 |
| 6,660,685 B1 | 12/2003 | Schussler | |
| 6,670,444 B2 | 12/2003 | Amendola | |
| 6,683,025 B2 | 1/2004 | Amendola | |
| 6,706,909 B1 | 3/2004 | Snover | |
| 6,713,201 B2 | 3/2004 | Bullock | |
| 6,723,072 B2 | 4/2004 | Flaherty | |
| 6,745,801 B1 | 6/2004 | Cohen | |
| 6,808,833 B2 | 10/2004 | Johnson | |
| 6,815,116 B2 | 11/2004 | Lenz et al. | 429/38 |
| 6,818,334 B2 | 11/2004 | Tsang | |
| 6,821,499 B2 | 11/2004 | Jorgensen | |
| 6,823,678 B1 | 11/2004 | Li | 62/3.5 |
| 6,828,049 B2 | 12/2004 | Bullock et al. | 429/23 |
| 6,834,632 B2 | 12/2004 | Kataoka | |
| 6,840,955 B2 * | 1/2005 | Ein | 607/108 |
| 6,849,351 B2 | 2/2005 | Hartnack | |
| 6,887,596 B2 | 5/2005 | Leban | |
| 6,916,159 B2 | 7/2005 | Rush | |
| 6,924,054 B2 | 8/2005 | Prasad | |
| 7,105,033 B2 | 9/2006 | Strizki | |
| 7,105,245 B2 | 9/2006 | Ohlsen | |
| 7,316,719 B2 | 1/2008 | Devos | |
| 7,645,536 B2 | 1/2010 | Akiyama | |
| 7,666,386 B2 | 2/2010 | Withers-Kirby | |
| 2002/0182459 A1 | 12/2002 | Hockaday | |
| 2003/0009942 A1 | 1/2003 | Amendola | |
| 2003/0037487 A1 | 2/2003 | Amendola | |
| 2003/0082427 A1 | 5/2003 | Prasad | |
| 2003/0138679 A1 | 7/2003 | Prasad | |
| 2003/0157389 A1 | 8/2003 | Kornmayer | 429/34 |
| 2003/0198558 A1 | 10/2003 | Nason | |
| 2004/0011662 A1 | 1/2004 | Xu | |
| 2004/0018415 A1 | 1/2004 | Lai et al. | 429/40 |
| 2004/0048135 A1 | 3/2004 | Hartnack et al. | |
| 2004/0052704 A1 | 3/2004 | Devos | |
| 2004/0062965 A1 | 4/2004 | Morse | |
| 2004/0062978 A1 | 4/2004 | Yazici | |
| 2004/0131903 A1 | 7/2004 | Shioya | |
| 2004/0148857 A1 | 8/2004 | Strizki | |
| 2004/0197214 A1 | 10/2004 | Arthur | |
| 2004/0202548 A1 | 10/2004 | Dai | |
| 2004/0211054 A1 | 10/2004 | Morse | |
| 2004/0211189 A1 | 10/2004 | Arnold | 62/3.5 |
| 2004/0229101 A1 | 11/2004 | Davis | |
| 2004/0240198 A1 | 12/2004 | Van Laar et al. | 362/105 |
| 2004/0253500 A1 | 12/2004 | Bourilkov | |
| 2005/0037252 A1 * | 2/2005 | Pham | 429/31 |
| 2005/0089415 A1 | 4/2005 | Cho | |
| 2005/0186871 A1 | 8/2005 | Hockaday | |
| 2005/0196666 A1 | 9/2005 | Gottesfeld et al. | |
| 2006/0127734 A1 | 6/2006 | McLean | |
| 2006/0196112 A1 | 9/2006 | Berry | |
| 2006/0275645 A1 | 12/2006 | Gallagher | |
| 2007/0020172 A1 | 1/2007 | Withers-Kirby | |
| 2007/0042244 A1 | 2/2007 | Spallone | |
| 2010/0150824 A1 | 6/2010 | Withers-Kirby | |

FOREIGN PATENT DOCUMENTS

| | | |
|---|---|---|
| JP | 2005-126877 | 5/2005 |
| JP | 2002/234358 | 1/2006 |
| WO | 04/001235 | 12/2003 |
| WO | 2004/062978 | 4/2004 |

OTHER PUBLICATIONS

Ying,Wu, "Hydrogen Storage via Sodium Borohydride: Current Status, Barriers & R&D Roadmap", Presentation presented at GCEP, Stanford University, Apr. 14-15, 2003.

* cited by examiner

ARTICLES OF CLOTHING AND PERSONAL GEAR WITH ON-DEMAND POWER SUPPLY FOR ELECTRICAL DEVICES

CROSS-REFERENCE TO RELATED APPLICATIONS

The present application claims priority from Provisional Patent Application with No. 60/569,340 filed on May 7, 2004, the entire content of which is incorporated herein by reference.

FIELD OF THE INVENTION

The present invention relates generally to fuel cell systems. More particularly the invention relates to articles of clothing and personal gear with on-demand power supply for electrical devices whereby the power is delivered by flexibly interconnected electrochemical (fuel cell) devices.

BACKGROUND

Nearly all-modern electronic devices require portable electrical power, and power consumption is often a performance bottleneck. Wireless products, such as personal digital assistants, mobile phones, entertainment devices, and next generation laptops in particular have a great demand for sustained power. For long-term, portable operation, fuel cells are an attractive solution. Fuel cells, like batteries, efficiently convert chemical energy into electricity, but have additional advantages, such as higher energy density and the possibility of instant refueling. Accordingly, it would be considered an advance in the art to develop new systems that allow for easy integration of fuel cells into our day-to-day operations and utilize them as an on-demand power supply for these power-hungry products.

SUMMARY OF THE INVENTION

The present invention provides new ways that allow for easy integration of fuel cells in our day-to-day operations and living. These integrated fuel cells can be utilized as an on-demand power supply for electrical devices or wireless products. In particular, the invention is an article of clothing with an on-demand power supply for one or more electrical devices. In one example the on-demand power supply is integrated at the inside of a jacket at the upper spine region. The integration of the on-demand power supply of the present invention is further useful to personal gear.

The power supply includes two or more stiff planar fuel cell devices that are distributed in a plane. The fuel cell devices are capable of delivering electrical power to one or more of the electrical devices carried by the person wearing the article of clothing. The number of fuel cell devices is dependent on the power requirements for the electrical devices.

The planar stiff fuel cells are flexibly interconnected in the plane by a flexible interconnecting means, which allows the stiff planar fuel cell devices to move with respect to each other out of the plane. This further allows the on-demand power supply to be nicely integrated in an article of clothing by a thin/flat design, i.e. it can be hidden away within or inside an article of clothing. The flexible means and the planar fuel cell devices are preferably distributed and sized with the objective to minimize negative impact to a body region or to the article of clothing.

The electrical and fuel connections between the fuel cells (and possibly other related components) are integrated with the flexible interconnecting means. Various examples are provided for the flexible interconnecting means such as: (i) one or more flexible joints or hinges, (ii) a flexible substrate onto which the stiff planar fuel cell devices are affixed and distributed, (iii) an extension from one of the plates of the two or more stiff planar fuel cell devices and of a thickness to allow for the necessary movement, or (iii) a flexible mold or laminate over the two or more stiff planar fuel cell devices.

To further integrate and increase ease of operation a control system is included to control the on-demand power supply or control different power levels for the electrical device(s). The control system could be integrated in the article of clothing, or could be a wireless remote control device that can be carried by the user. In a one embodiment, wires are integrated with the article of clothing (e.g. by passing through the material of a jacket) to the electrical device or to the control system (if applicable).

BRIEF DESCRIPTION OF THE DRAWINGS

The objectives and advantages of the present invention will be understood by reading the following detailed description in conjunction with the drawings, in which:

FIGS. 4-5 each show an example of a stiff planar fuel cell according to the present invention.

DETAILED DESCRIPTION

Although the following detailed description contains many specifics for the purposes of illustration, anyone of ordinary skill in the art will readily appreciate that many variations and alterations to the following exemplary details are within the scope of the invention. Accordingly, the following preferred embodiments of the invention are set forth without any loss of generality to, and without imposing limitations upon, the claimed invention.

Figure 1:
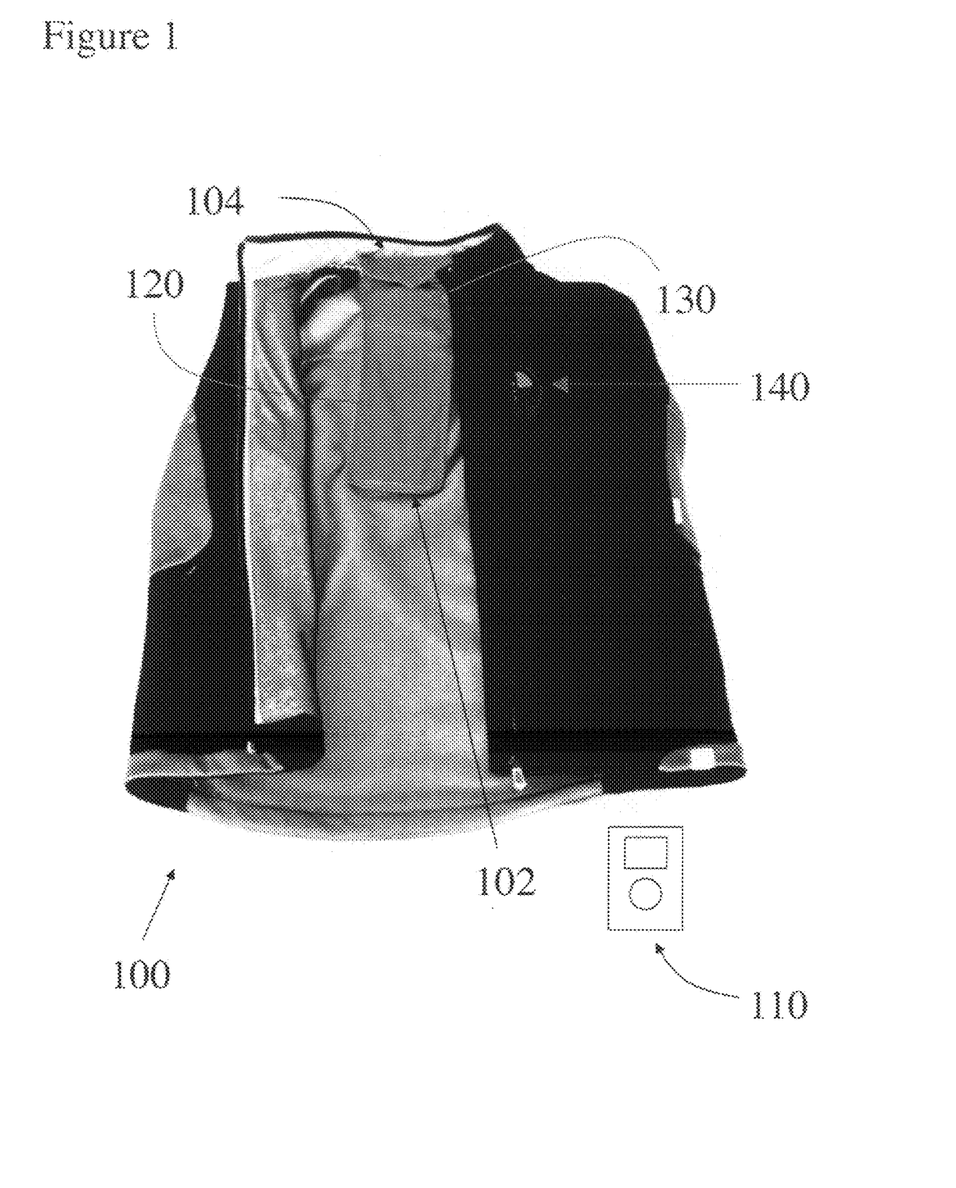
FIG. 1 shows an example of a jacket with an on-demand power supply according to the present invention.
Figure 2:
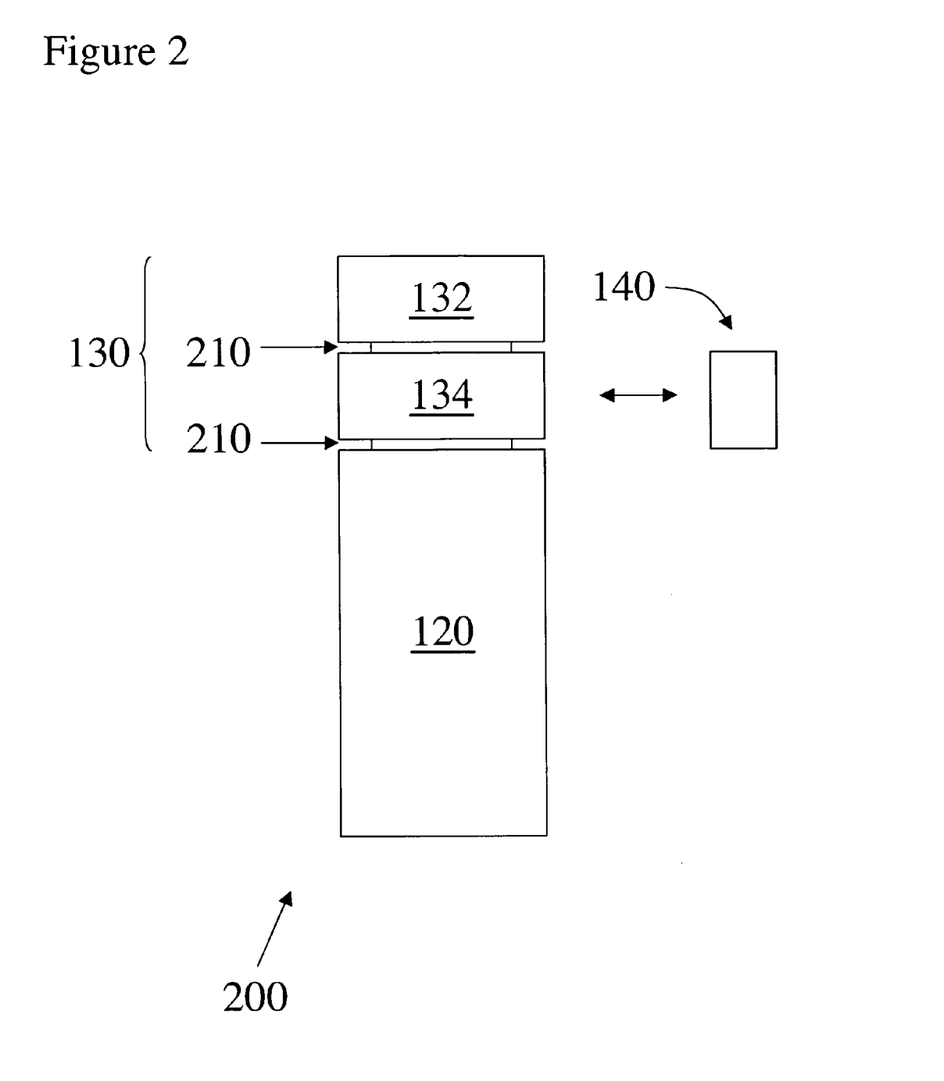
FIG. 2 shows a schematic example of an on-demand power supply according to the present invention.

FIG. 1 shows an example of an article of clothing, i.e. a jacket 100, with an on-demand power supply for one or more electrical devices 110. The power supply of the present invention includes two or more stiff fuel cell devices 120 that are distributed in a plane and placed in e.g. a pocket 102 of jacket 100. The number of stiff planar fuel cells in the plane depends on the power and voltage requirement. Other parts 130 of the on-demand power supply are at least a fuel source 134 and a balance of plant 132 that are integrated 210 with the fuel cell devices 120 as further shown by on-demand power supply 200 in FIG. 2. The definition of stiff related to the planar fuel cells is such that minimal deformation occurs during normal use. Stiff planar fuel cells have advantages over fully flexible fuel cells in that they are less likely to be damaged by over bending (bending the fuel cell at a radius small enough to cause damage to the cell) and fatigue (repeated bending at one location). Additionally, the associated manifolding and compression associated with stiff fuel cells tends to enable higher performance (in terms of power per unit area) than fully flexible fuel cells. Semi-flexible fuel cells (fuel cells with flexible interconnects) improve fully flexible fuel cells by enabling more comfortable and functional integration into flexible products.

In the present example of FIG. 1, the on-demand power supply is placed, through an opening at top, inside pocket 102. One objective here is to have the largest/broadest plane of the fuels cells facing the body or a body region. In this example the largest plane of the on-demand power supply is facing the upper spine region. Another objective in the design and integration with an apparel is to develop the on-demand power supply as thin as possible so that it can be easily integrated, e.g. hidden away in the apparel, while meeting the power requirements as desired by the user to power one or more of the electrical devices. A flap 104 could be used to close the opening of the pocket 102.

The preferred location of the on-demand power supply is where it would minimize negative impact to a body region, or to the movement of the body region or the jacket. Examples of such body regions are the upper spine region or the rib cage area, or even parts of the arms in case smaller on-demand power supplies are used. In general, it could be placed anywhere where a user desires and is not limited to a pocket at the upper spine region.

The fuel cell devices in the present system are electrochemical devices delivering a power density ranging from 0.05 Watt to 1 Watt per $cm^2$. The number of planar fuel cells in the on-demand power supply electrically connected in series will determine the total output voltage. The power density and active area of fuel cell membrane will determine the total power output of the system. Each individual cell will contribute 0.3-0.8 Volts, wherein the total voltage output is determined by the number of cells connected in series.

Figure 3:
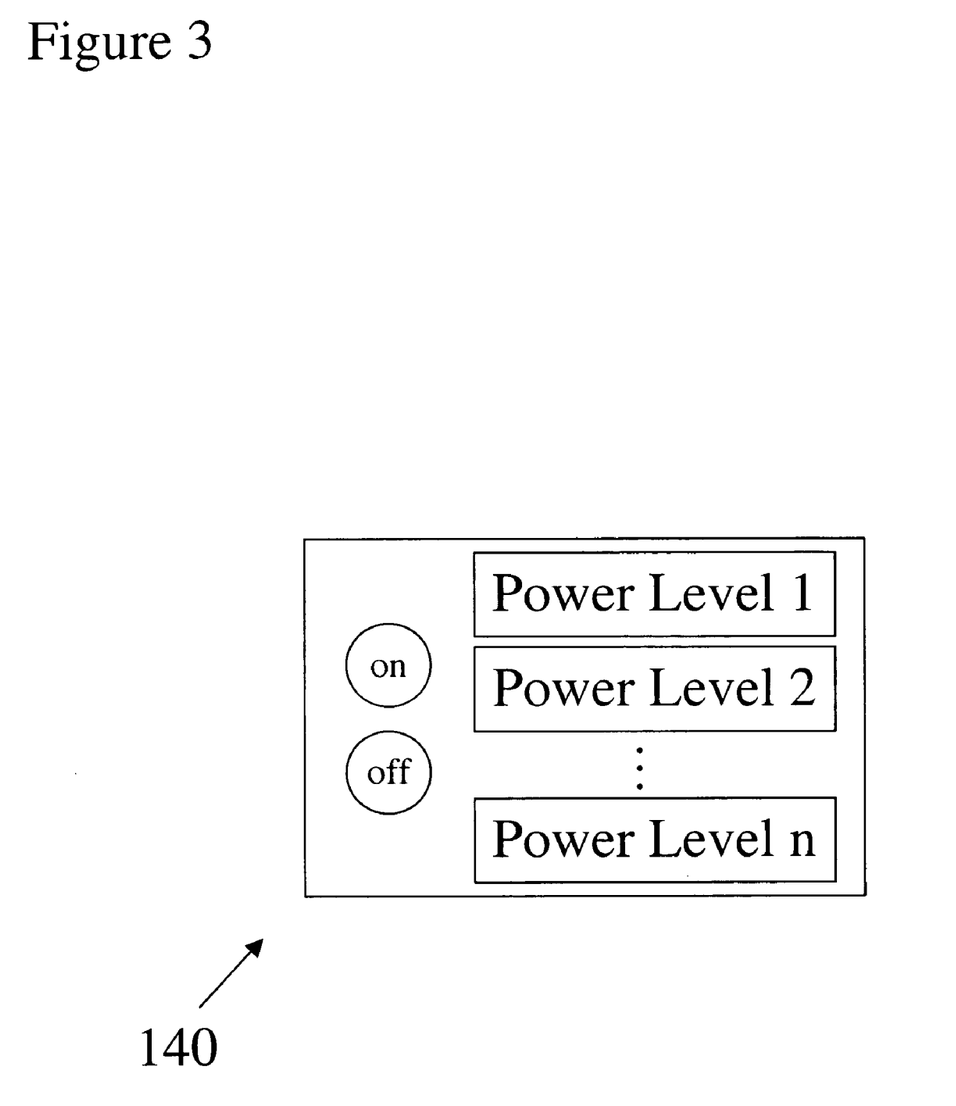
FIG. 3 shows an example of a control system according to the present invention.

A control system 140 to control the power could either be integrated with the on-demand power supply or positioned in a convenient location to the user. In one example control system 140 is integrated in jacket 100 as illustrated in FIG. 1, either as a remote wireless control system to a user or as a wired control system. The control could be as simple as an on/off mechanism or could have a more sophisticated control loop that sets a particular power level, such as Power level 1, Power level 2 . . . Power level n as shown in FIG. 3. Control system 140 could also include a display to provide feedback on the state or performance of the on-demand power supply. The power output of the fuel cell is controlled by varying the electrical load on the cells. This can be done by a variety of methods including varying the duty cycle of an intermittent connection between the fuel cell and the load element (Pulse Width Modulation Control) or by varying the resistance of the load element.

The electrical power transfer between the on-demand power supply and the electrical device is established via wires that are preferably passing through the article of clothing or personal gear. Similarly the wires between the control system and the balance of plant are preferably hidden or tucked away in the article in case the control system is not setup as a wireless unit.

To ensure integration of the on-demand power supply in an article of clothing and at the same time maximizing the comfort of wearing such a system to the user, the stiff planar fuel cell devices are distributed and spaced in a plane by flexible interconnecting means. The key objective of the flexible interconnecting means is to allow the stiff planar fuel cell devices to move with respect to each other out of the plane so as to minimize negative impact to (i) a body region by following anatomical features, or (ii) to the movement of the body region or the jacket. In case of personal gear the flexible interconnecting means allows movements of the gear. The flexible interconnecting means has either integrated therein or therewith the electrical connections and fuel connections for each of the stiff planar fuel cell devices, which is described herein according to several examples.

Figure 4:
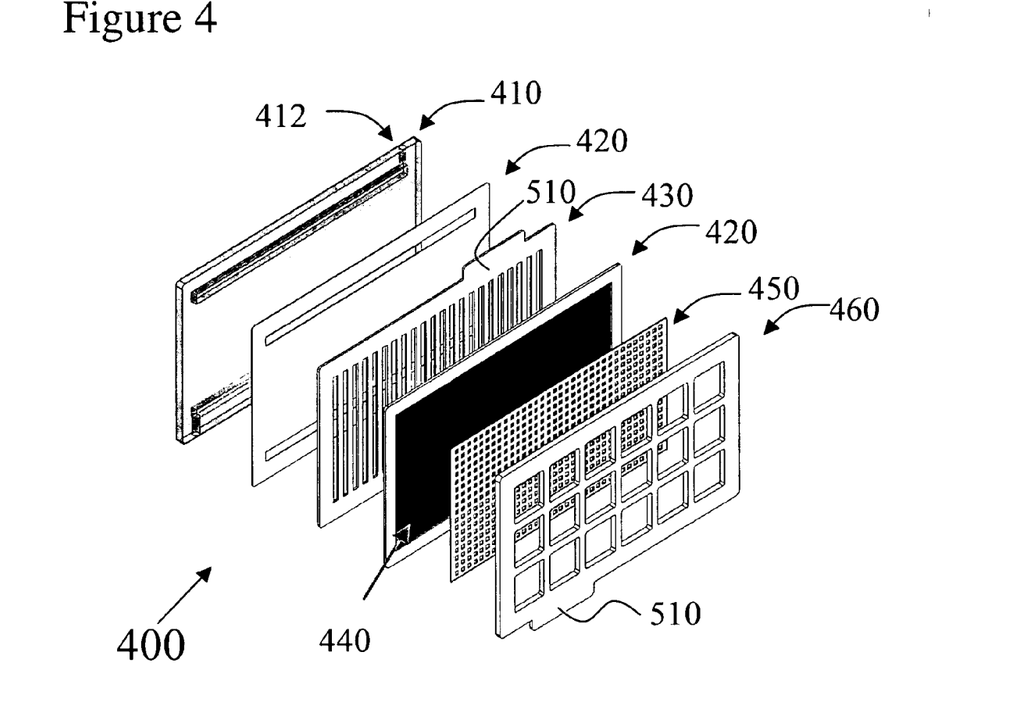
Figure 5:
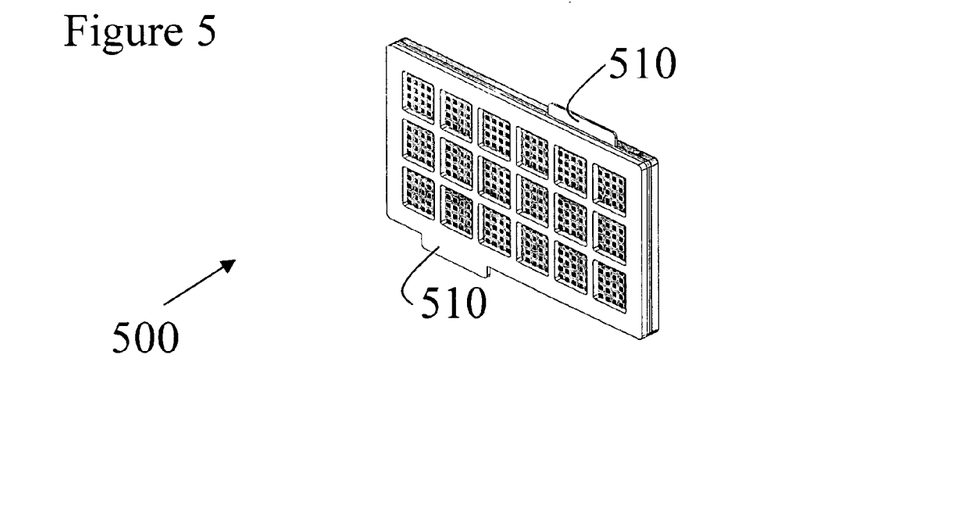
FIG. 5 shows an example of two or more stiff planar fuel cell devices flexibly interconnected according to the present invention.

FIG. 4 shows an exploded view 400 of a planar stiff fuel cell with several plates or layers. The planar fuel cell distinguishes a hydrogen gas manifold 410 with a fuel (hydrogen port) 412 and two layers of a bonded adhesive 420, 422 at either side of an anode plate 430. Bonded adhesive layer 422 has disposed thereon a membrane and electrode assembly (MEA) 440 over which a conductive mesh 450 is placed. At the other outside of the planar fuel cell a cathode plate 460 is placed against and over the conductive mesh 450. FIG. 5 shows the assembled stiff planar fuel 500 with two electrical tabs 510 that are used to electrically connect with other fuel cells and eventually with the balance of plant before it connected to an electrical device.

Figure 6:
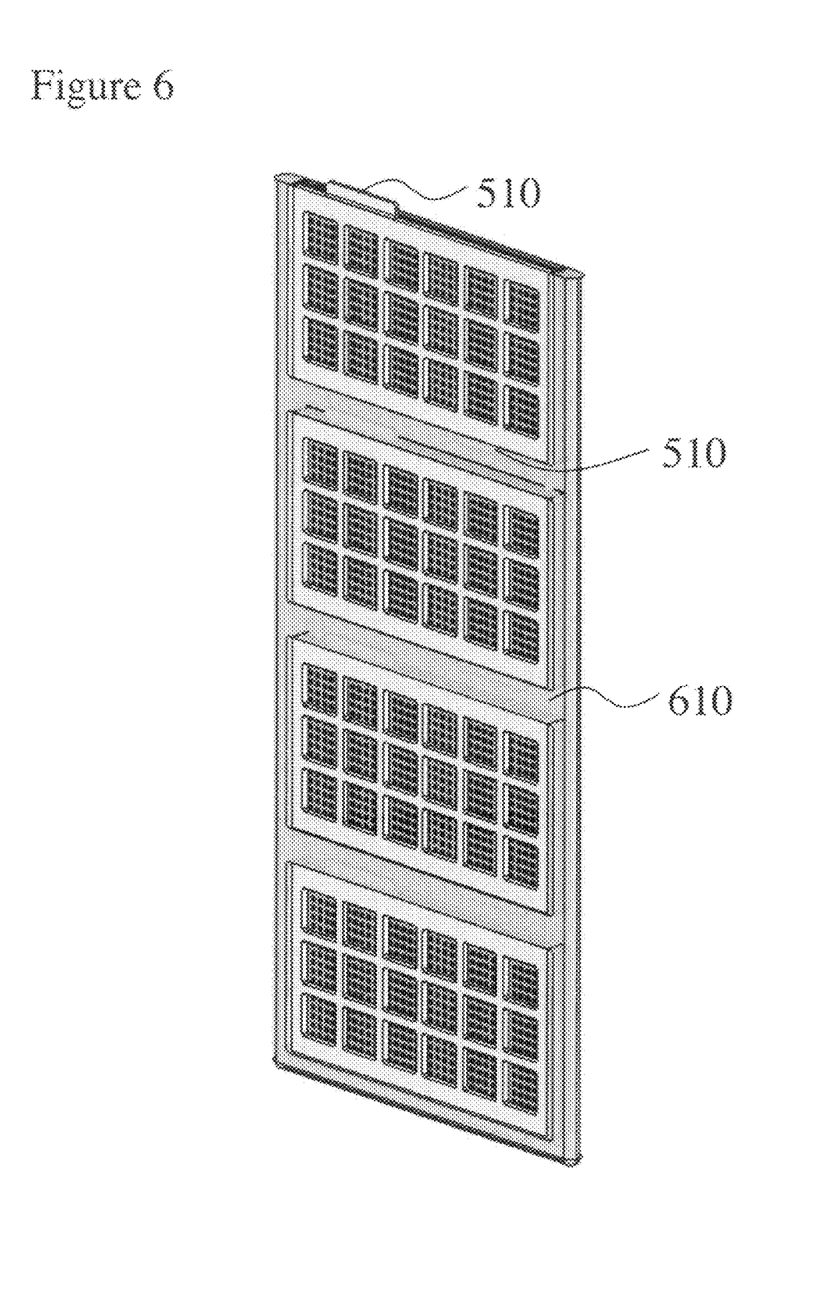
FIG. 6 shows an example of four stiff planar fuel cells interconnected by flexible means according to the present invention.

FIG. 6 shows an example of four stiff planar fuel cells 500 interconnected by flexible means 610, which could be a flexible material that is molded over the fuel cells to create flexible joints in between them. Another objective of the flexible interconnecting means is to include the electrical connection and fuel connections in between the fuel cells, adding strain relief as well as a nicely integrated package with wires or fuel lines hidden as much as possible.

Figure 7:
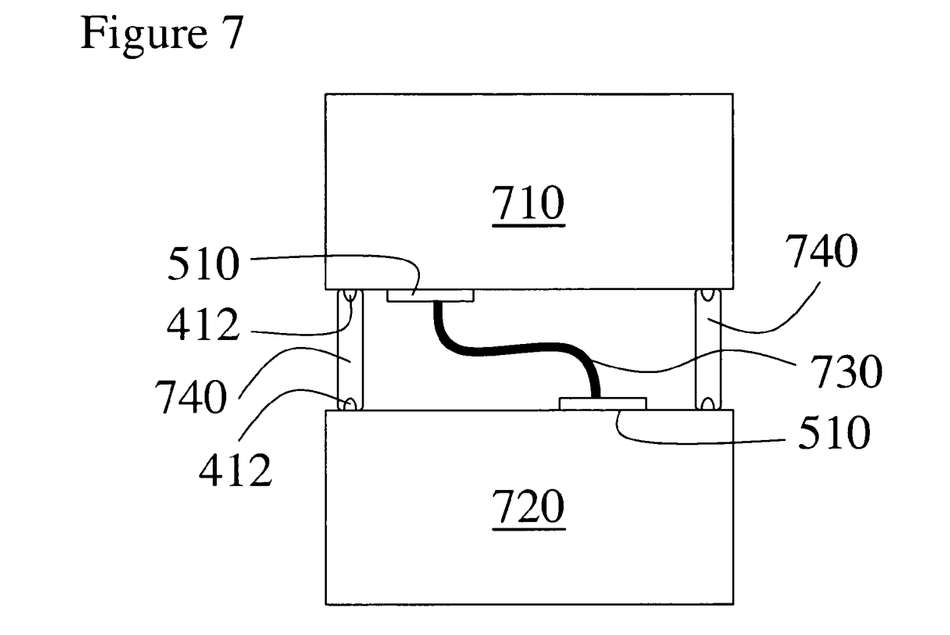
FIGS. 7-8 each show an example of electrical and fuel connections between planar fuel cells according to the present invention.
Figure 8:
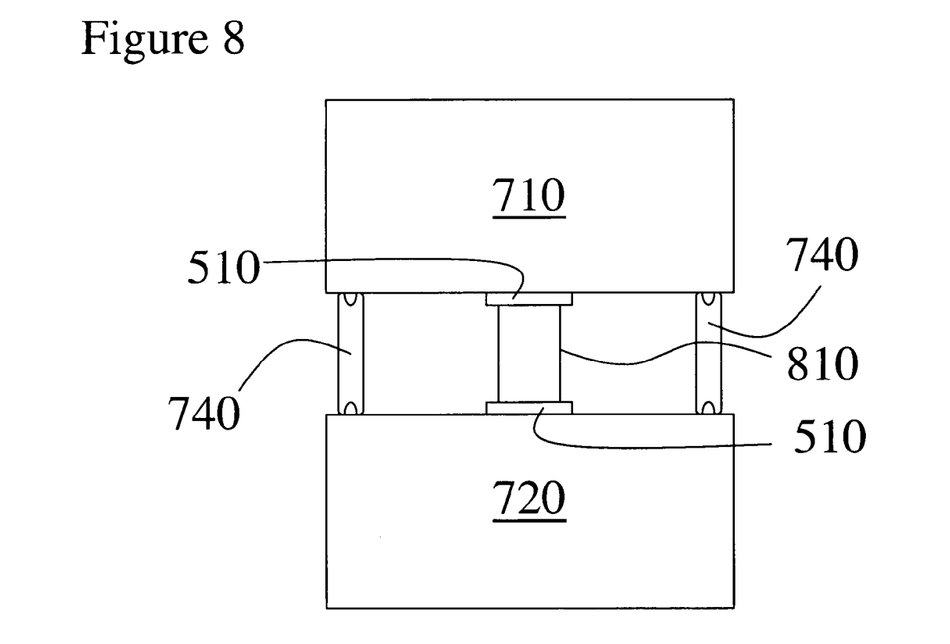

FIGS. 7-8 show some examples of serially connecting the fuel lines and electrical contacts for two planar fuel cells 710, 720. The key objective here is to use materials or designs that maintain the flexibility of the flexible interconnecting means. Therefore, one example could be a flexible wire 730 connecting the two electrical connections 510 of two respective fuel cells. In another example shown in FIG. 8, a flexible metal foil 810 could be used to electrically connect the two electrical connections 510. A person of average skill in the art to which this invention pertains can appreciate that other flexible electrically conducting mechanism or connections can be used. The present invention is therefore not limited to these two exemplary electrical connections.

Figure 9:
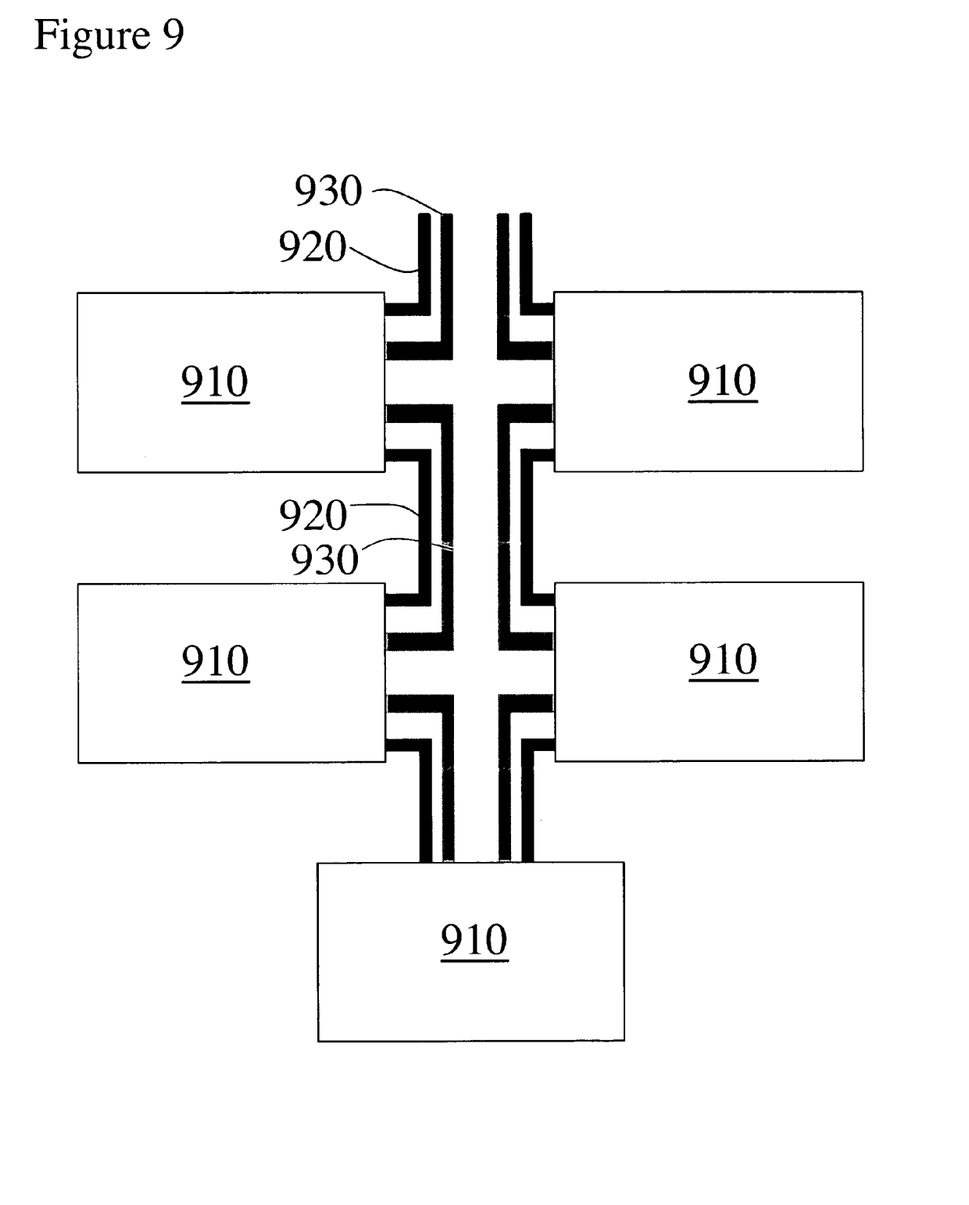
FIG. 9 shows an example of five planar fuel cell devices distributed in a plane according to the present invention.

The fuel connections 740 could also range from a variety of designs and materials such as a flexible fuel line tightly connected to the fuel ports 412. In another example one or more flexible or stiff fuel connectors could be used that are movably connected to the fuel ports 412, e.g. by adding joints or hinges. FIG. 9 shows an example of a configuration of five stiff planar fuel cells 910 and their arrangements for electrical connections 920 and fuel connections 930. A person of average skill in the art to which this invention pertains can appreciate that various different configurations can be designed that are all within the scope of the invention.

Figure 10:
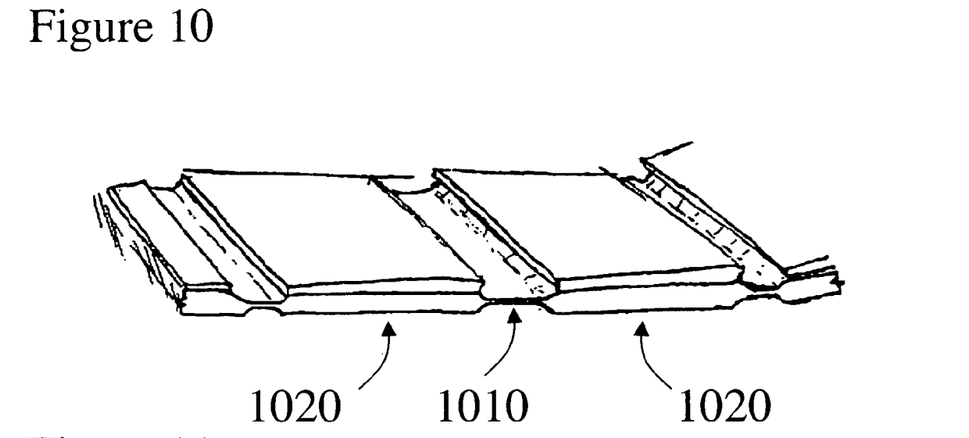
FIGS. 10-13 show examples of flexible interconnecting means according to the present invention.
Figure 11:
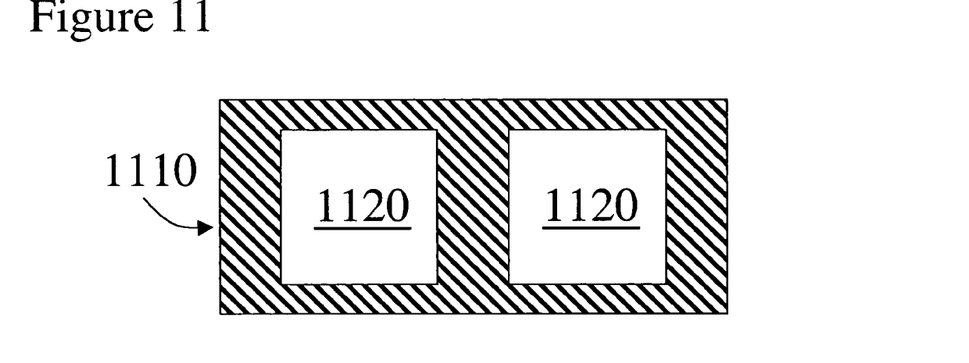
Figure 12:
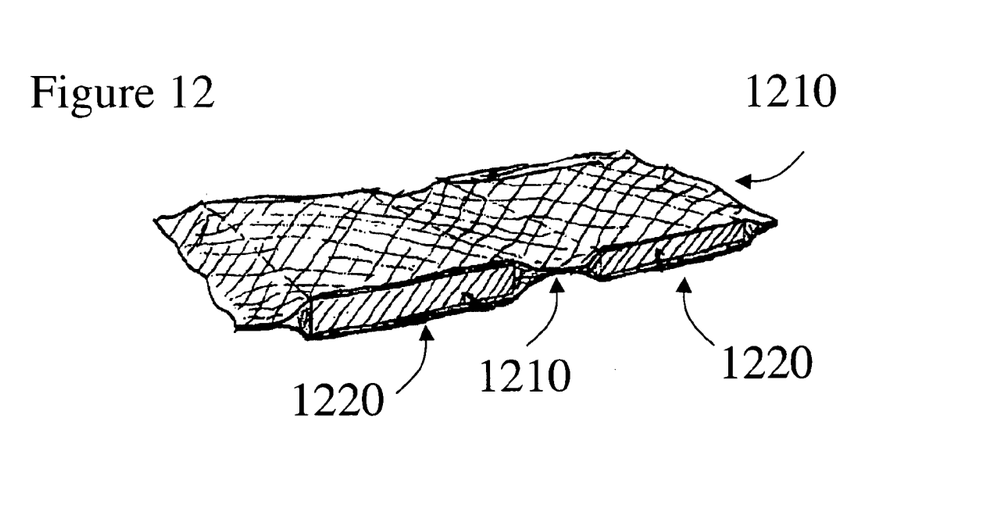
Figure 13:
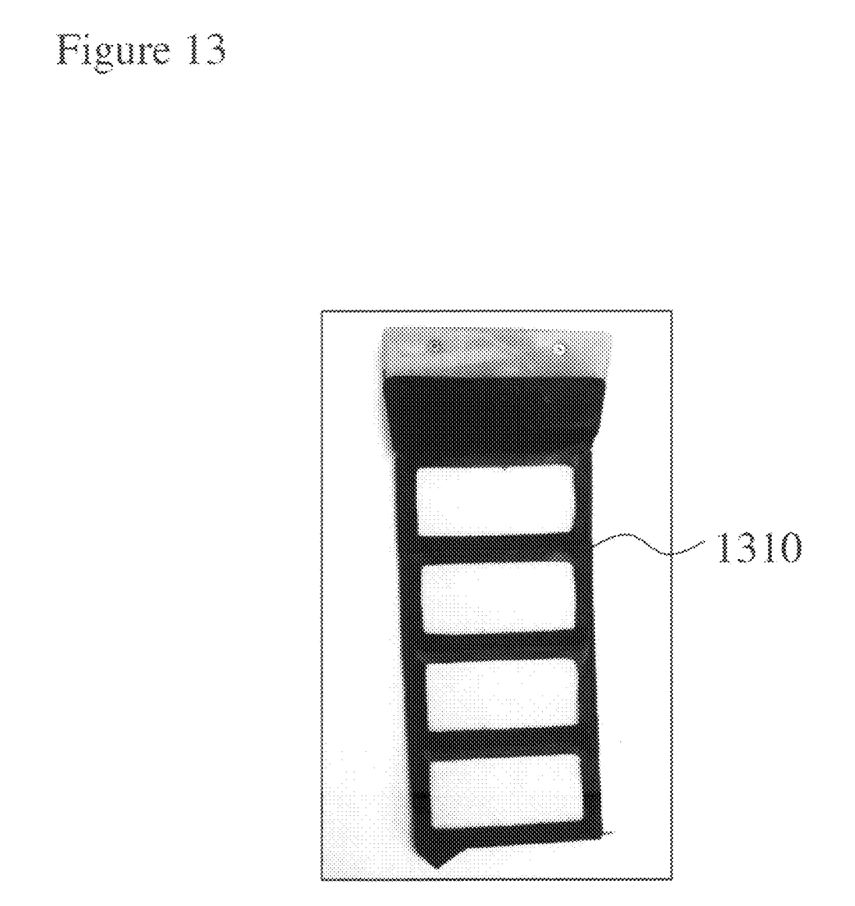

The flexible interconnecting means includes a variety of different ways to ensure (i) a flexible connection between the stiff planar fuel cells, (ii) integration of fuel and electrical connections, and (iii) strain relief for these connections. In one aspect, one or more flexible joints could be used. In another aspect, the fuel and electrical connection could by themselves provide the flexible interconnecting means (FIGS. 7-9). In yet another example joint or hinges 1010 could be added to provide the flexibility between fuel cells 1020 as shown in FIG. 10. In another aspect, a flexible substrate 1110 could be used onto which the two or more stiff planar fuel cell devices 1120 are affixed and distributed as shown in FIG. 11. In yet another aspect, the flexible interconnecting means could be an extension from one of the plates of the fuel cell (e.g. the anode plate) whereby the thickness of the plate is adjusted (e.g. thinned or patterned) so that the flexibility is enabled in between the fuel cells; this could be envisioned by 1010 and 1110 in FIGS. 10-11). As shown in FIG. 6, in still another aspect of the invention the flexible interconnecting means could be established by a molding or laminating over the two or more stiff planar fuel cell devices. Such a mold or laminate could for example be a fabric 1210 as is shown in FIG. 12 where it covers fuel cells 1220. However, in general, the flexible interconnecting means could be established by a variety of methods and flexible materials including, but not limited to, fabrics, flexible polymers (e.g. urethane), rubber, leather, metals, and polymer coated fabrics. FIG. 13 shows an example of the on-demand power supply system of the present invention integrated within flexible interconnecting means 1310.

The fuel cells could be integrated into an article by a number of possible methods. The fuel cells cell may be affixed to an article (e.g. a fabric) by methods including, but not limited to, hook and loop connectors, adhesives, magnets, enclosing them in a pocket sewn into the fabric or removably attachments (e.g. one or more buttons or hooks, Velcro, a zipper, or any other equivalent mechanism or combinations thereof), adhering a fabric layer to the fuel cells and then sewing the perimeter of the fabric layer into the garment, sandwiching the cell between layers of fabric, welding a fabric layer bonded to the cell to the fabric of the garment, or any other magnetic, mechanical, or chemical connectors. In one embodiment, the garment could be offered to a user with the on-demand power supply permanently integrated into the jacket (such that the fuel cartridge may be changed). In another embodiment, the article could be offered to a user with features such that the system could be easily integrated in other applications or apparel. Such features may include, but are not limited to, special pockets for the fuel cell and generators, Velcro attachment points, and embedded wires and/or interface controls.

The on-demand power supply could be used in a wide variety of articles of clothing or personal gear and applications thereof including, but not limited to, apparel integrated personal climate control (both heating and cooling), apparel integrated health monitoring devices, sports equipment (e.g., skis, snowboards), medical devices, wearable computing devices, augmented reality devices, apparel embedded safety devices such as lights, foldable/rollable power sources (e.g., power supplies for life rafts, tents), apparel integrated communication devices, and portable electronics battery chargers or any other portable power and/or heat sources.

There are a large number of possible applications for the on-demand power supply described above. Three classes of applications include, but are not limited to, using the fuel cell system solely as a source of electrical power, using it for the purpose of combined heat and electrical power, and solely for the purpose of a controllable heat source. Possible applications include, but are not limited to, using the fuel cell system in an article of clothing, sporting equipment, survival equipment, bedding, medical devices, luggage, backpacks, seating, or material transport.

When integrated into an article of clothing, this system could be used for applications including, but not limited to, personal climate control, heated apparel, health monitoring, communications, lighting, powered exoskeleton systems, and powering or recharging electronic devices. Specific embodiments for heated apparel include, but are not limited to, heated jackets, vests, shirts, pants, gloves, mittens, hats, socks, boots, shoes, and goggles. One embodiment for the application of heated shoes and boots is to use a fuel cell and or generator as part of the sole of the shoe or boot.

Examples of sporting equipment or personal gear applications include, but are not limited to, heated skis and snowboards, and heated ski and snowboard bindings. Examples of survival equipment include, but are not limited to, electrical power and heat for life rafts, heated bivouac bags, and climate controlled tents. Bedding products that could benefit from the fuel cell system described include, but are not limited to, heated sleeping bags, heated sleeping pads, heated blankets, and heated pillows.

Examples of possible medical device products include supplying heat and electric power to patient temperature control devices, and supplying electric power to wearable health monitoring devices. Two possible specific examples of patient temperature control and monitoring devices include a transport device for babies and a transport device for trauma victims. Incorporated into backpacks or other luggage, the fuel cell system could be used for climate control of the wearer or the contents of the luggage or for supplying electrical power to a number of possible electronic devices. An example of a seating application for this technology includes, but is not limited to, heated stadium seat pads or other heated seating devices.

The fuel cell may be integrated into a wide variety of clothing including, but not limited to, outer jackets, inner layers, vests, gloves, hats, pants, socks, shoes, and boots.

Some types of fuel cells are differentiated by their electrolytes—Solid Oxide Fuel Cells, Molten Carbonate Fuel Cells, Alkaline Fuel Cell, Polymer Electrolyte Membrane Fuel Cell, and Phosphoric Acid Fuel Cells. In some embodiments, hydrogen fueled Polymer Electrolyte Membrane (PEM) or PEM fuel cells are used in the application of integrating a fuel cell into flexible form factors. There are a number of alternatives in the design of a PEM fuel cell including the gas distribution material and layout, gas flow structure design, and sealing method, to name just a few. However, it is noted that the present invention uses stiff planar fuel cells rather than a continuous flexible planar fuel cell to maintain high performance and efficiency of the on-demand power supply.

While many alternatives could be used, a substantially flat fuel cell has a number of advantages for integration into products with flexible form factors. With the broad face oriented towards the body, such a cell could be worn with minimal extra bulk or discomfort to the user. When used for the application of heated clothing, such a design would maximize the transfer of heat from the fuel cell to the user. As described above, such a cell could be held together by adhesive bonding around the edges, functioning to seal the gas inside the cell and maintain contact pressure between the electrodes and the charge collectors on the gas distribution plates. A further advantage of using a flat fuel cell for this application is that the system could be either shaped to fit the area of the body that it rests against, or it could be made flexible, so that it conformed to the body of the user as described above.

Oxygen can be supplied to the cathode of the fuel cell by a number of different methods. Alternatives include, but are not limited to, pure oxygen from a contained oxygen source, compressed air from an air compressor, forced flow using a fan, and "free air" breathing using convection and natural air flow to supply fresh air. The choice of oxygen supply affects the power output of the cell and the number of additional components necessary to make the cell functional. Free air breathing cells tend to have the lowest power output per unit area of the cell (currently 150 mW/cm²), but have the advantage of requiring the fewest additional components for operation. For power outputs of approximately 50 Watts and below, free air breathing cells are used in some embodiments for this application. However, in instances where the cathode cannot be exposed to the atmosphere (eg. Divers), higher power outputs are required, or a source of moving air may easily be incorporated into the design (such as when used for cooling via a compressor), or other alternatives may become the preferred embodiment.

Although the present invention and its advantages have been described in detail, it should be understood that the present invention is not limited to or defined by what is shown or discussed herein. The drawings, description and discussion herein show examples of the invention and provide examples of using the invention. One skilled in the art will realize that implementations of the present invention could be made without departing from the principles, spirit or legal scope of the present invention. Accordingly, the scope of the present invention should be determined by the following claims and their legal equivalents.

What is claimed is:

1. An apparatus with on-demand power supply for an electrical device, comprising:
   a. an article of clothing having an interior surface;
   b. two or more stiff planar fuel cell devices, distributed in a plane, that deliver electrical power to one or more electrical devices, wherein a broad face of each planar fuel cell device is substantially aligned in the plane; and
   c. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices;
   c. wherein the fuel cell devices are removably coupled to the article of clothing substantially near the interior surface of the article of clothing, wherein the plane formed by the fuel cell devices substantially parallels the interior surface of the article of clothing, and wherein the fuel cell devices are polymer electrolyte membrane fuel cells.

2. The apparatus as set forth in claim 1, wherein said flexible interconnection and said planar fuel cell devices are distributed and sized to minimize negative impact to a body region or to said article of clothing.

3. The apparatus as set forth in claim 1, wherein said two or more stiff planar fuel cell devices are integrated to the article of clothing at a rear torso-covering region of the article of clothing.

4. The apparatus as set forth in claim 1, further comprises a control system to control said on-demand power supply or control a power level for said electrical device.

5. The apparatus as set forth in claim 1, further comprising a control system integrated in said article of clothing.

6. The apparatus as set forth in claim 1, further comprising wires passing through said article of clothing to said electrical device or to a control system.

7. The apparatus of claim 2, wherein the fuel cell devices heat the body region.

8. The apparatus of claim 3, wherein the fuel cell devices integrate to the jacket by reversibly sliding into a pocket on the interior surface of the article of clothing.

9. An apparatus for a living organism, the apparatus with on-demand power supply for an electrical device, comprising:
   a. an article of personal gear;
   b. two or more stiff planar fuel cell devices, distributed in a plane, that removably couple to the article of personal gear to heat a body region of the organism and deliver electrical power to one or more electrical devices, wherein each of said planar fuel cells devices is an electro-chemical device; and
   c. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices; wherein the fuel cell devices are removably coupled to the article of personal gear by fitting into a pocket disposed on the interior surface of the article of personal gear, and wherein the fuel cell devices are polymer electrolyte membrane fuel cells.

10. The apparatus as set forth in claim 9, further comprising a control system to control said on-demand power supply or a power level for said electrical device.

11. The apparatus as set forth in claim 9, further comprising a control system integrated in said article of personal gear.

12. The apparatus as set forth in claim 9, further comprising wires passing through said article of personal gear to said electrical device or to a control system.

13. An article of clothing with on-demand power supply for an electrical device, comprising:
   a. two or more stiff planar fuel cell devices, distributed in a plane, that deliver electrical power to one or more electrical devices, wherein a broad face of each of the planar fuel cell devices is substantially aligned in the plane; and
   b. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices; wherein the planar fuel cell devices integrate into the article of clothing by reversibly enclosing the fuel cell devices into a pocket located on the interior of an upper rear torso-covering region of the article of clothing, and wherein the fuel cell devices are polymer electrolyte membrane fuel cells.

14. The article of clothing of claim 13 further including a control system that controls the power output of the fuel cell devices and is electronically coupled to one of the fuel cell devices.

15. The article of clothing of claim 13, wherein the flexible interconnection comprises of a flexible fuel line and a wire.

* * * * *

UNITED STATES PATENT AND TRADEMARK OFFICE
CERTIFICATE OF CORRECTION

PATENT NO.        : 8,062,797 B2
APPLICATION NO.   : 11/124401
DATED             : November 22, 2011
INVENTOR(S)       : Fisher et al.

Page 1 of 1

It is certified that error appears in the above-identified patent and that said Letters Patent is hereby corrected as shown below:

In Claim 1, the "c." label before "wherein the fuel cell devices" should be removed as follows:

c. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices;
[[c.]] wherein the fuel cell devices are removably coupled to the article of clothing substantially near the interior surface of the article of clothing, wherein the plane formed by the fuel cell devices substantially parallels the interior surface of the article of clothing, and wherein the fuel cell devices are polymer electrolyte membrane fuel cells.

Section c) should read:

c. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices;
wherein the fuel cell devices are removably coupled to the article of clothing substantially near the interior surface of the article of clothing, wherein the plane formed by the fuel cell devices substantially parallels the interior surface of the article of clothing, and wherein the fuel cell devices are polymer electrolyte membrane fuel cells.

Signed and Sealed this
Twenty-ninth Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,062,797 B2  
APPLICATION NO. : 11/124401  
DATED : November 22, 2011  
INVENTOR(S) : Fisher et al.

Page 1 of 1

It is certified that error appears in the above-identified patent and that said Letters Patent is hereby corrected as shown below:

Column 7, line 38 (Claim 1, line 15) the "c." label before "wherein the fuel cell devices" should be removed as follows:

c. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices;
[[c.]] wherein the fuel cell devices are removably coupled to the article of clothing substantially near the interior surface of the article of clothing, wherein the plane formed by the fuel cell devices substantially parallels the interior surface of the article of clothing, and wherein the fuel cell devices are polymer electrolyte membrane fuel cells.

Column 7, lines 38-44, Section c) should read:

c. at least one flexible interconnection for interconnecting said two or more stiff planar fuel cell devices, said flexible interconnection allowing said stiff planar fuel cell devices to move with respect to each other out of said plane, and said flexible interconnection having integrated therein or therewith electrical connections and fuel connections for each of stiff planar fuel cell devices;
wherein the fuel cell devices are removably coupled to the article of clothing substantially near the interior surface of the article of clothing, wherein the plane formed by the fuel cell devices substantially parallels the interior surface of the article of clothing, and wherein the fuel cell devices are polymer electrolyte membrane fuel cells.

This certificate supersedes the Certificate of Correction issued May 29, 2012.

Signed and Sealed this  
Nineteenth Day of June, 2012

David J. Kappos  
*Director of the United States Patent and Trademark Office*